(12) United States Patent
Singh et al.

(10) Patent No.: US 9,636,179 B2
(45) Date of Patent: May 2, 2017

(54) SURGICAL DRAPE SYSTEM FOR UROLOGY PROCEDURES ON MALE PATIENTS

(75) Inventors: Errol O. Singh, Columbus, OH (US); Ake A. Hellstrom, Columbus, OH (US)

(73) Assignee: Ohio Urologic Research, LLC, Columbus, OH (US)

( * ) Notice: Subject to any disclaimer, the term of this patent is extended or adjusted under 35 U.S.C. 154(b) by 352 days.

(21) Appl. No.: 13/983,995

(22) PCT Filed: Feb. 8, 2012

(86) PCT No.: PCT/US2012/024246
§ 371 (c)(1),
(2), (4) Date: Sep. 20, 2013

(87) PCT Pub. No.: WO2012/109306
PCT Pub. Date: Aug. 16, 2012

(65) Prior Publication Data
US 2014/0007886 A1    Jan. 9, 2014

Related U.S. Application Data

(60) Provisional application No. 61/441,267, filed on Feb. 9, 2011.

(51) Int. Cl.
*A61B 19/08* (2006.01)
*A61B 46/20* (2016.01)
*A61B 46/00* (2016.01)

(52) U.S. Cl.
CPC ............ *A61B 19/087* (2013.01); *A61B 46/20* (2016.02); *A61B 46/30* (2016.02)

(58) Field of Classification Search
CPC ........................ A61B 19/087; A61B 2019/084
See application file for complete search history.

(56) References Cited

U.S. PATENT DOCUMENTS

| 2,842,130 A | 7/1958 | Seidler |
| 3,799,161 A | 3/1974 | Collins |
| (Continued) | | |

FOREIGN PATENT DOCUMENTS

| CN | 201036566 | 3/2008 |
| GB | 1 500 009 | 11/1974 |
| (Continued) | | |

*Primary Examiner* — Tarla Patel
(74) *Attorney, Agent, or Firm* — Standley Law Group LLP

(57) ABSTRACT

A simple surgical drape system of generally flat shape for male urology procedures that provides full isolation of top versus bottom surface by a sealing fenestration surrounding the meatus area. It is achieved by manually forming the flat drape to a tent-like shape around the penis with a fenestration aperture smaller than glans diameter, supported by and sealing to the glans tip, and then attaching a penile clamp to hold the drape. This allows a simplified safer antibacterial preparation and less chance of infection complications. The sealed design permits better management of urology liquids, and can use absorption pad on drape top side. The drape wrinkles act as a penile position stabilizer, reducing need for extended use of the one operator hand for penile support. Drape is removable with catheter in place.

33 Claims, 12 Drawing Sheets

(56) References Cited

U.S. PATENT DOCUMENTS

| | | | |
|---|---|---|---|
| 4,588,397 A * | 5/1986 | Giacalone | A61F 5/453 |
| | | | 604/349 |
| 4,622,962 A | 11/1986 | Kauffman | |
| 4,834,711 A | 5/1989 | Greenfield et al. | |
| 4,903,710 A | 2/1990 | Jessamine et al. | |
| 5,238,009 A | 8/1993 | House | |
| 5,275,177 A * | 1/1994 | Wilk | A61M 25/002 |
| | | | 128/849 |
| 5,388,593 A | 2/1995 | Thomalla | |
| 5,795,334 A | 8/1998 | Cochrane, III | |
| 6,705,324 B1 * | 3/2004 | Petersvik | A61B 17/0293 |
| | | | 128/849 |
| 6,966,320 B1 * | 11/2005 | Baynes | A61B 19/08 |
| | | | 128/849 |
| 7,299,803 B2 | 11/2007 | Kovac et al. | |
| 2004/0254512 A1 * | 12/2004 | Paturu | A61B 46/20 |
| | | | 602/43 |
| 2005/0115570 A1 | 6/2005 | Hare et al. | |
| 2006/0207609 A1 * | 9/2006 | Gil | A61B 46/20 |
| | | | 128/849 |
| 2007/0175487 A1 | 8/2007 | Eid | |
| 2008/0236598 A1 * | 10/2008 | Gobel | 128/849 |
| 2009/0277460 A1 * | 11/2009 | Carrez | A61B 19/08 |
| | | | 128/853 |
| 2010/0145314 A1 | 6/2010 | Hazan | |
| 2010/0192960 A1 | 8/2010 | Rotolo | |

FOREIGN PATENT DOCUMENTS

| | | |
|---|---|---|
| GB | 2 372 451 A | 8/2002 |
| WO | 81/02515 A1 | 9/1981 |
| WO | 2009/012336 A1 | 1/2009 |

* cited by examiner

SURGICAL DRAPE SYSTEM FOR UROLOGY PROCEDURES ON MALE PATIENTS

REFERENCE TO RELATED APPLICATION

This application claims benefit of provisional application 61/441,267, filed Feb. 9, 2011.

BACKGROUND OF THE INVENTION

This invention is in the technical field of medical equipment, in particular for surgical drape systems utilized in urology procedures on male patients. Such procedures are relatively common but still have demonstrated less than desired outcome in many cases. Problems may arise with infections and patient discomfort that require prolonged patient care and procedure re-work in best cases, but can in worse cases introduce serious long term consequences both for patients and care givers. This occurs currently despite more stringent medical guidelines being in place. There is a very active demand today by the entire society to reduce health care cost, and medical procedure infections and other procedure complications is one important factor.

As part of preparation for urology procedures like catheterization, the patient is scrubbed with antibacterial agents in the entire pubic area. This process has the drawback that this particular area is typically covered with body hair and has several skin folds, resulting in risk for incomplete bacteria elimination. Furthermore, loose hair and skin particles from this area may easily become dislodged during the urology procedure and can contaminate instruments or the urethral meatus and nearby areas. This may call for using extra potent antibacterial agents. However, increasing the amount, or potency, of antibacterial agents can lead to the long term drawback of breeding more resistant bacteria strains.

In the male urology procedure, the patient is typically cleaned and prepared, and then covered at least partially with a sterile surgical drape. The drape may use multiple sections or have one or more fenestrations included to access to the male organ. It is common that sizeable amounts of liquids emerge from the urethra or instruments during the procedure. Such liquids may however flow down through fenestration apertures and reach other parts of the patient body and the operating table, causing inconvenience and a less clean environment. Medical spent liquids disposal also needs special procedures and equipment to avoid spills or undesired contact.

At urethral catherization or endoscopy, proper insertion and control of the instrument is critical to avoid tissue damage or patient discomfort. This is complicated by the need to use one of the hands to fully support the penis which is typically flaccid. One of the operator's hands may be in use to support the penis during most of the procedure of current art, making it inconvenient to perform other duties during the process.

Sometimes it is necessary to let catheters or other connected instruments remain in the patient for an extended time after the procedure. This requires a drape design that can be easily removed with instruments in place. Condom-like male drape features would not be practical for this.

The prior art known to the present inventors can be divided into two main categories of male urological surgical drapes. First, there are the flat drapes containing one or more fenestrations for accessing the penis, and second, there are the condom or sheath-containing male surgical drapes.

The above-referenced drawbacks have been attempted to be solved to varying degree by prior art, but there is our knowledge not any solutions disclosed that solves of all these issues with one surgical drape system and minimum drawbacks.

SUMMARY OF THE INVENTION

The present invention is a drape system for reduced risk and simplified urological procedures for male patients. The drape system isolates the pelvic area as a non-sterile environment below the drape and a sterile area above the drape, with a sealed fenestration between these areas preventing contamination from below to reach the top side and urology fluids to reach the bottom side. The exposed patient area on the top sterile side is limited to only the urethral meatus with small surroundings of the glans tip, and provides a seal from the non sterile areas below. This simplifies antibacterial preparation of the patient ahead of the urological procedure and reduces infection risk by isolating the urology procedure entry location from the general pubic area.

The drape may have a simple, generally flat shape made of flexible translucent plastics or a thin elastic sheet material. It is draped around the penis in an initially tent-like fashion and held in place by means of a surrounding penile drape clamp. A removable drape cover will upon removal expose only a small area around the meatus for antibacterial preparation and accessible for urology procedures.

This penile protruded shape draping starting from a flat shape creates longitudinal drape wrinkles that can actually improve the drape functionality. An unexpected observation is that the longitudinally rippled shape of the drape may act as an external penile stiffening structure connected to the surrounding drape for stabilized penile positioning even in a flaccid state. This reduces the need for the operator to manually hold the penis in position and therefore occupying one hand during most of the urological procedure.

Because this drape design creates a sealed area above the patient except the meatus area, control and collection of urology liquids is simplified. For instance, a disposable and safe to handle absorbing or liquid gelling pad may be placed on portions of drape top side.

Removal of the drape after the urology procedure with instruments like catheters still in place can be achieved by a splittable line in the drape all the way in from an external drape edge and in to the fenestration. This is simple to achieve due to the generally flat sheet design of the drape, compared to the difficult to split molded drape protrusions in some prior art.

As a summary, this male patient urology drape system can offer major advantages in safety, functionality, simplicity, ease of doing procedures and cost versus prior art

DETAILED DESCRIPTION OF THE INVENTION

The purpose of the invention is easiest clarified by first a brief comparison to prior art.

Figure 1:
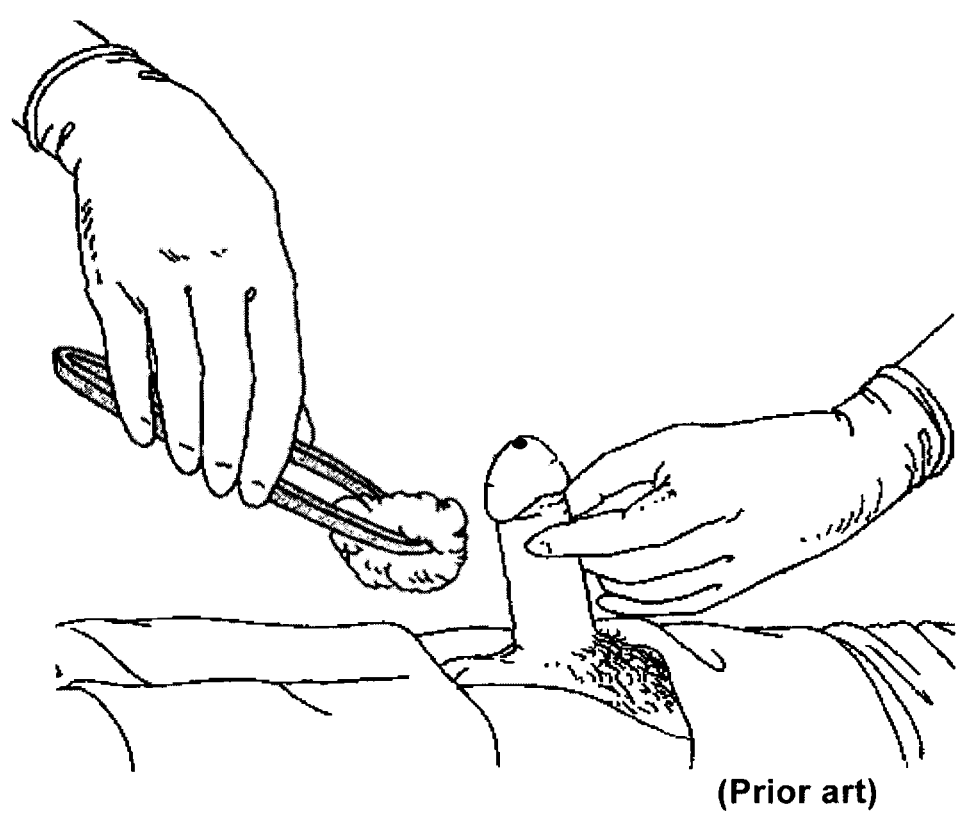
FIG. 1 shows a representation of antibacterial cleaning in prior art.

FIG. 1 (prior art) shows a male patient being prepared by antibacterial swab before a urological procedure according to prior art. The whole exposed genital area must be treated. It is noted that exposed body hair and skin folds will create crevices that may harbor particles and bacteria that is difficult to fully reach with the swab.

Figure 2:
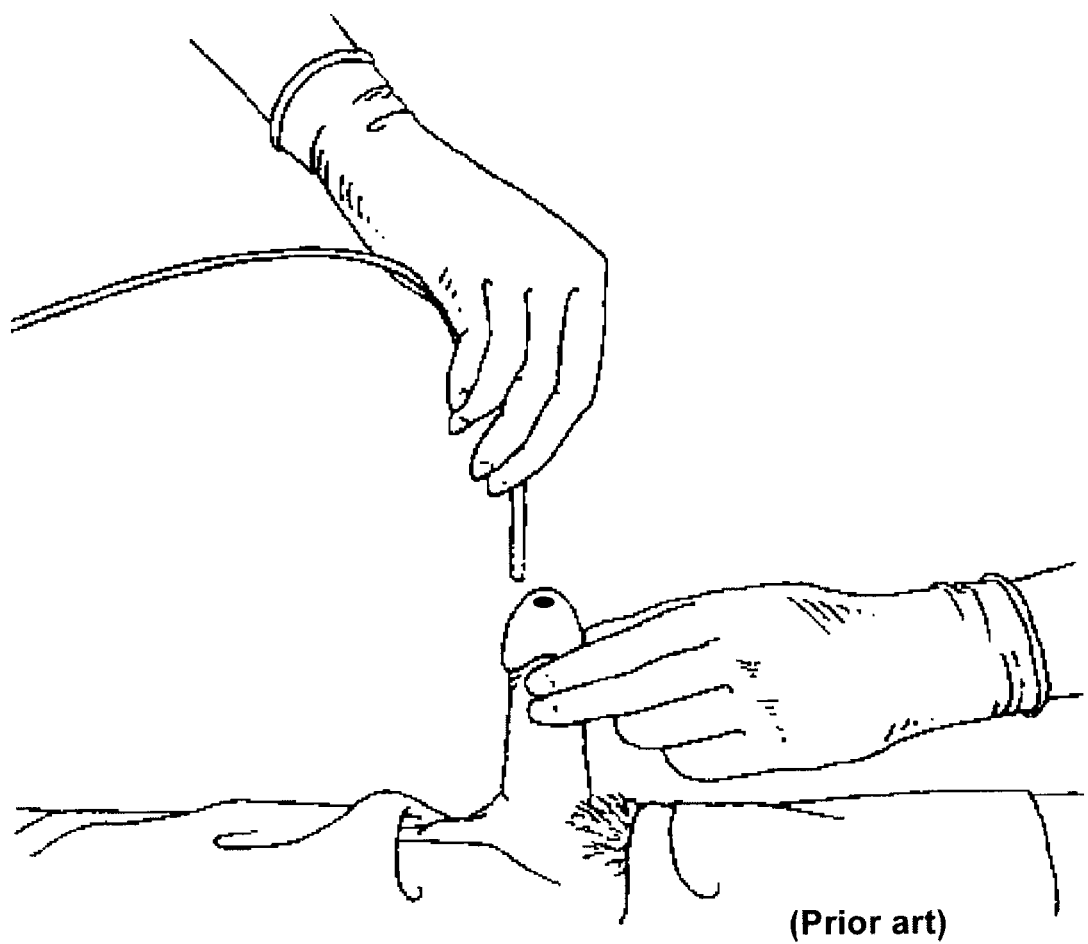
FIG. 2 shows a urological procedure in prior art

FIG. 2 (prior art) shows a catherization or similar urology procedure performed according to prior art. It is noted that hair or particles in the genital area may become dislodged during the process and reach the meatus, or the operator's sterile gloves, or insertable urology instruments. It is also noted that the usually flaccid penis must be supported by hand during the process, or it may fall down and reach contamination. Furthermore, the need for one hand providing support during most of the process makes it inconvenient for the operator to do other duties during the procedure. It is also noted that due to the open path to the pubic area, liquids emerging from the patient or from treatment may flow down under the drapes and onto the patient and operating table.

Figure 3:
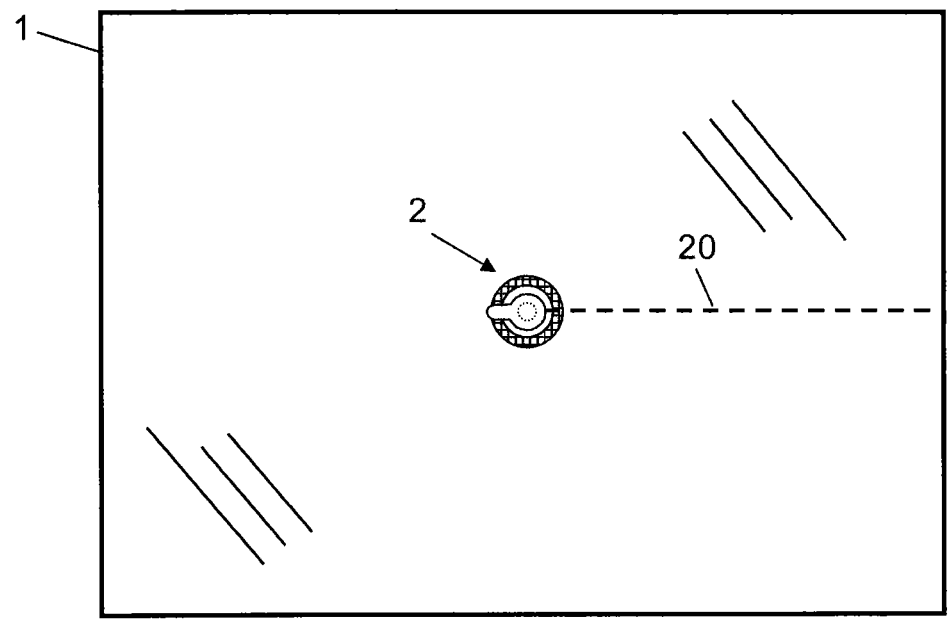
FIG. 3 shows a planar view of the drape of the invention
Figure 4:
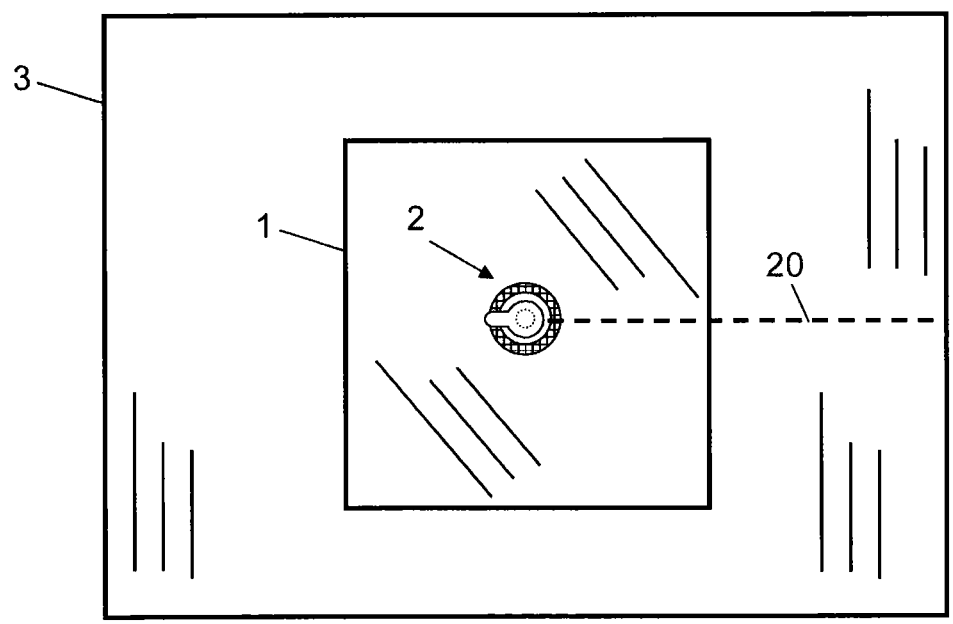
FIG. 4 shows a planar view of the drape of including a different material insert

The invention drape system is shown in FIG. 3 and includes a drape 1 with a fenestration 2 and a split line 20. The drape 1 may be made of a transparent material, for instance clear plastics, or by a thin elastic film, for instance latex. The purpose of the fenestration and the split line will be explained in subsequent paragraphs. The shape of the drape can be planar and rectangular as shown, but may he cut to any shape or formed to fit the patient and also include additional features known from prior art. Thus, the shape of the drape can be non-rectangular, such as circular. In FIG. 4 is shown a variation of the design where the drape 1 is attached in a sealed fashion to a surrounding larger drape sheet 3 that is made of a different material, for instance textile, non-wovens, or opaque plastics.

The drape 1, preferably translucent, can be transparent. In the embodiment of FIG. 4, surrounding sheet 3, for example formed of standard medical non-woven disposable material, can be more opaque than central translucent sheet 1, providing a feeling of privacy for the patient.

The translucent sheet 1 is constructed from readily available plastic film used in the medical field, for example, vinyl (such as polyvinyl chloride), polyethylene, polypropylene, polycarbonate, polyester, silicone elastomer, acetate and so forth film materials. In selecting a film material for use as sheet 1, factors such as the softness of the film, the ease of application of the film when used as a male drape, adaptability of the film to body contour, patient comfort and wrinkle stiffening properties of the film can be evaluated. For example, a 3 mil (0.070 mm) soft grade vinyl film can be used for construction of sheet 1. Sheet 1 may be constructed of plastic film used in forming prior art drape materials, for example, plastic film of about 1 to 5 mil (0.025 to 0.125 mm) in thickness. A sheet made of soft material may need to be made thicker than a drape made of a harder grade material in order to provide similar stiffening effects.

The male drape of the present invention must be sterile as packaged and remains sterile until use. The inventive drape can be uncoated or completely or partially coated or impregnated with agents known in the art, such as antibacterial, adhesive and sealing compounds.

Figure 5:
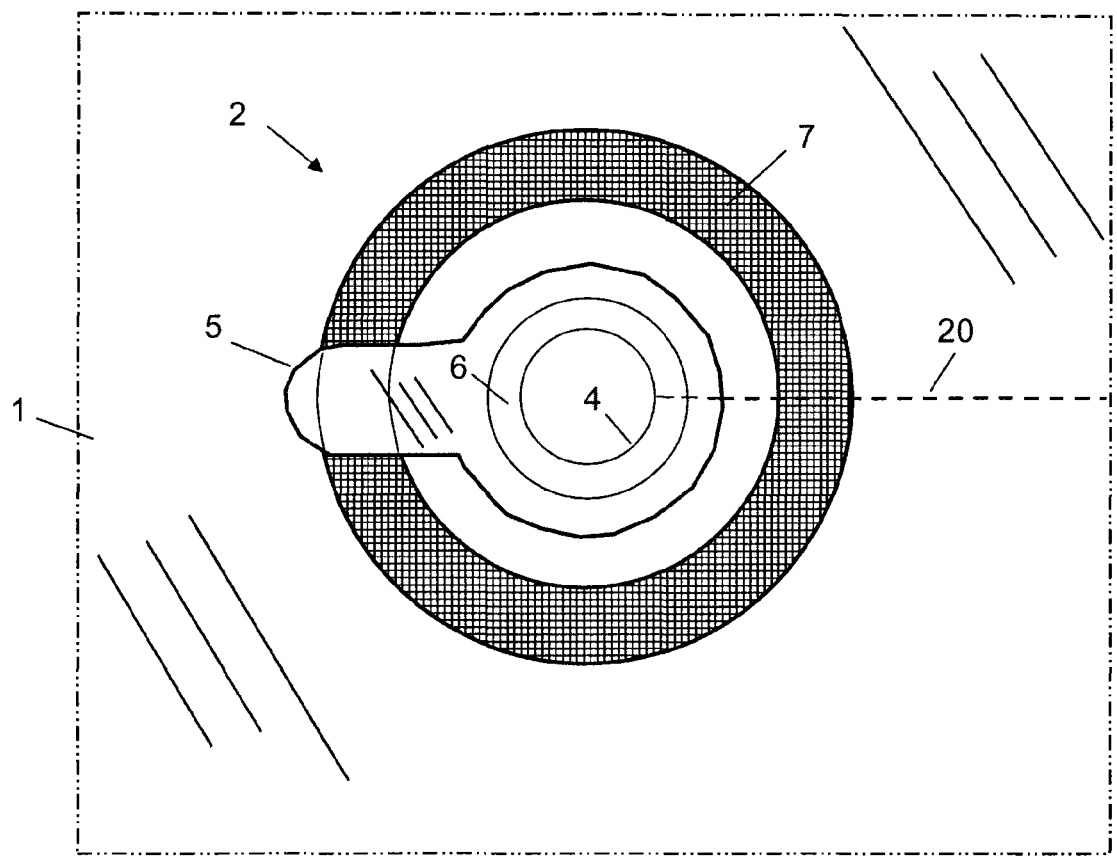
FIG. 5 shows an enlarged planar view of the fenestration in the drape
Figure 6:
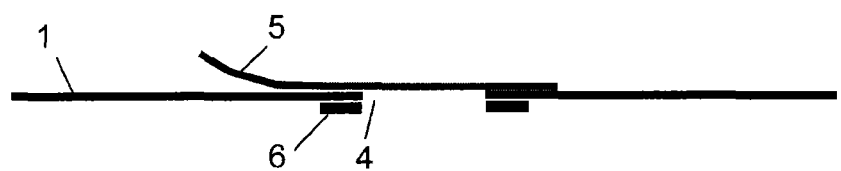
FIG. 6 shows a cross section of the fenestration in which the seal ring has substantially the same inside diameter as the diameter of the fenestration

FIG. 5 is an enlarged and more detailed description of the fenestration 2 with a planar view on the top side away from the patient, while FIG. 6 shows a cross section. The drape 1 includes a generally circular aperture 4 that is initially covered by a pull-away capable cover 5. This is preferably made of a transparent thin material for operator see-through, or it may be made of stretchable thin film like latex. The cover 5 may be attached and sealed to the drape 1 by means of a temporary adhesive, and shaped with a finger tab for manual removal. Additionally, the aperture 4 in the drape 1 may also have a seal ring 6 or 16 attached around the aperture 1 to provide seal to the male body parts as will be explained later, and also for reinforcement of the aperture. The inside diameter of the aperture 4 and the seal ring 6 or 16 are chosen to be smaller than the diameter of the male glans such that it will rest on the glans without full penetration.

The sealing ring 6 or sealing ring 16 that is attached to the drape 1 can be formed of a material which possess the same degree of flexibility and rigidity as, or be softer or more rigid than the film material used for sheet 1. For example, sealing ring 6 or sealing ring 16 may be die cut from a soft sheet material or molded as a more rigid plastic material. Soft sealing ring materials may provide better patient comfort while still functioning as an adaptable gasket. On the other hand, harder sealing ring materials provide a greater dimensional stability. Routine experimentation will provide a sealing ring possessing a balance of desired properties. For example, the sealing ring 6 or sealing ring 16 may be constructed of a silicone elastomer, or could be made of a soft sponge-like material. It may furthermore be made of a homogeneous material or coated or infused with antibacterial or liquid sealing agents.

Figure 14:
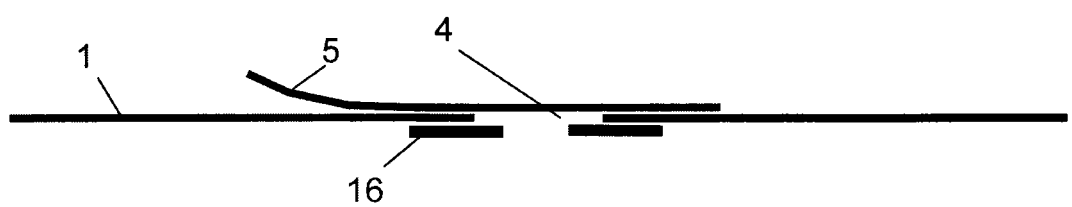
FIG. 14 shows a cross section of the fenestration in which, as compared to the embodiment depicted in FIG. 6, the seal ring has a smaller inside diameter than the diameter of the fenestration.

The degree of partial penetration of the male glans by drape aperture 4 and by sealing ring 6 as depicted in FIG. 6 in which the diameter of aperture 4 and inside diameter of sealing ring 6 are substantially identical, can vary with the diameter of the patient's glans. FIG. 14 depicts an embodiment of the invention distinct from the embodiment of FIG. 6. In FIG. 14, the sealing ring 16 has a smaller inside diameter than the diameter of drape aperture 4. By selecting a soft and elastic material for construction of sealing ring 16 in the FIG. 14 arrangement, a flexible seal is provided that will accommodate a wide range of glans diameters, because the sealing ring 16 will elastically deform to the glans contour.

In FIG. 5 is also shown a marking 7 that can be printed or attached on the drape 1 to enable the operator to quickly locate the fenestration 2 on the drape, which will be of particular value if both the drape 1 and the cover 5 are made of translucent materials.

Now referring to FIGS. 7, 8, 9, 10 and 11, these show a suitable sequence in applying the drape 1 onto a patient and prepare the patient for the urological procedure.

Figure 7:
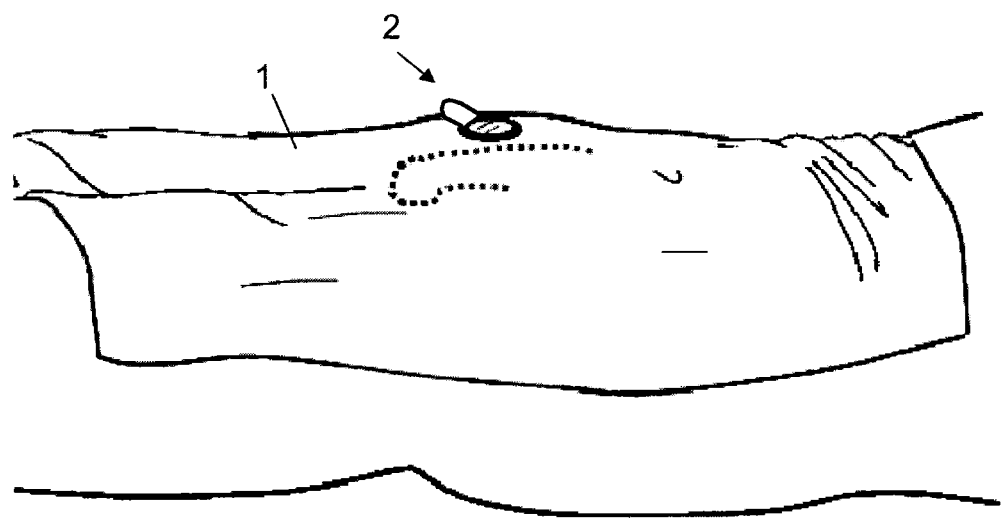
FIG. 7 shows the first step, a drape laid down on a male patient

FIG. 7 shows the drape 1 that is laid over the patient with the cover 2 away from the patient. The drape 1 will from now on isolate the non-sterile patient area on the bottom side from the sterile and sealed top side of the drape 1.

Figure 8:
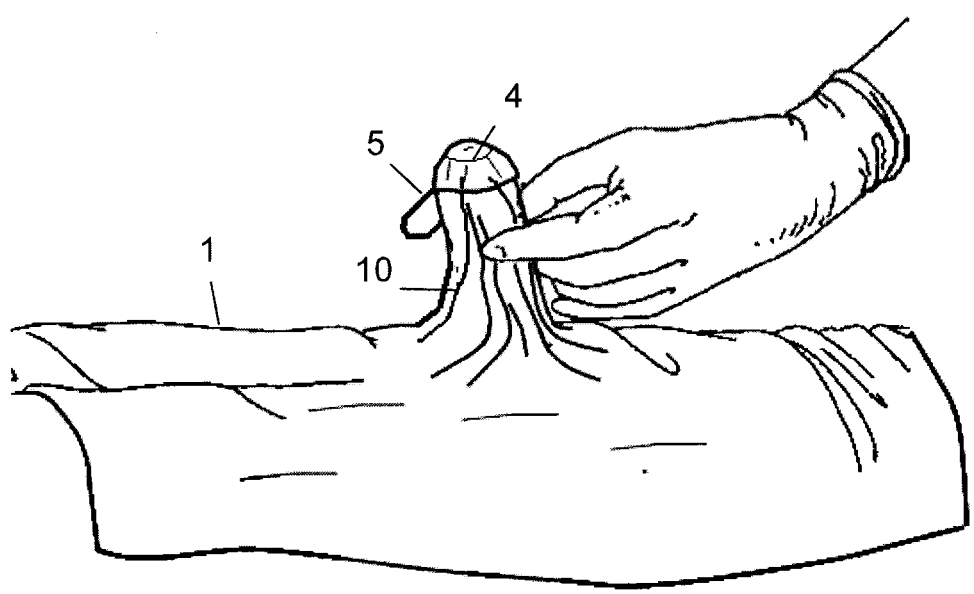
FIG. 8 shows the drape formed to shape by hand

FIG. 8 shows the drape 1 being positioned around the penis in an initially tent like shape such that the cover 5 and the sealed aperture 4 are approximately centered over the urethral meatus. This can be done by vision through a translucent drape or cover, or via tactile feel through a thin elastic and less translucent drape. By this procedure, the drape 1 will form wrinkles 10 that are essentially longitudinal to the penis. These wrinkles will be most evident and hard if the material in the drape 1 is of moderate thickness, and smaller in effect if the material in drape 1 is very thin and elastic. The presence of these wrinkles provides an unexpected and simple means of penile positioning that will be further explained in later paragraphs.

Figure 9:
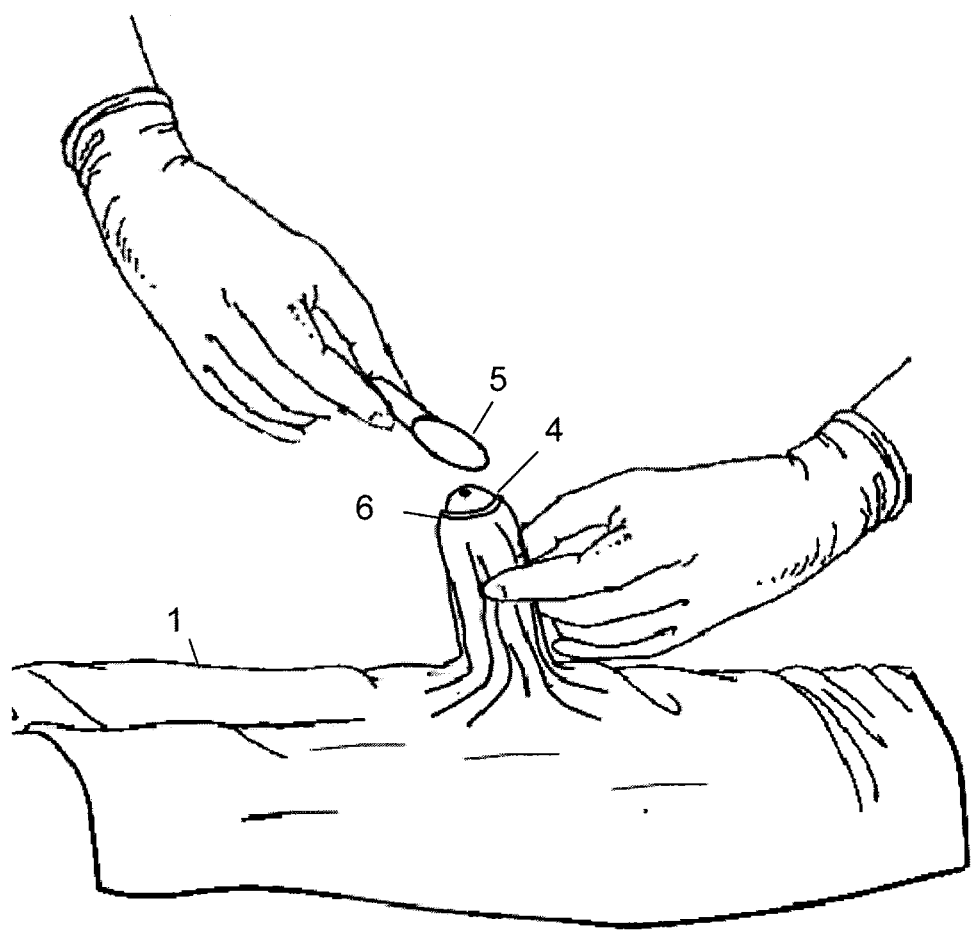
FIG. 9 shows the drape protective cover removed

FIG. 9 shows the removal of the cover 5 from the drape 1, exposing the urethral meatus approximately in center of the aperture 4. The diameter of the aperture 4 is less than the diameter of the patient's glans, making the seal ring 6 resting and sealing against the glans tip surrounding the meatus. The use of seal ring 6 is optional depending on the softness and edge characteristics of drape 1 to perform the sealing task.

Figure 10:
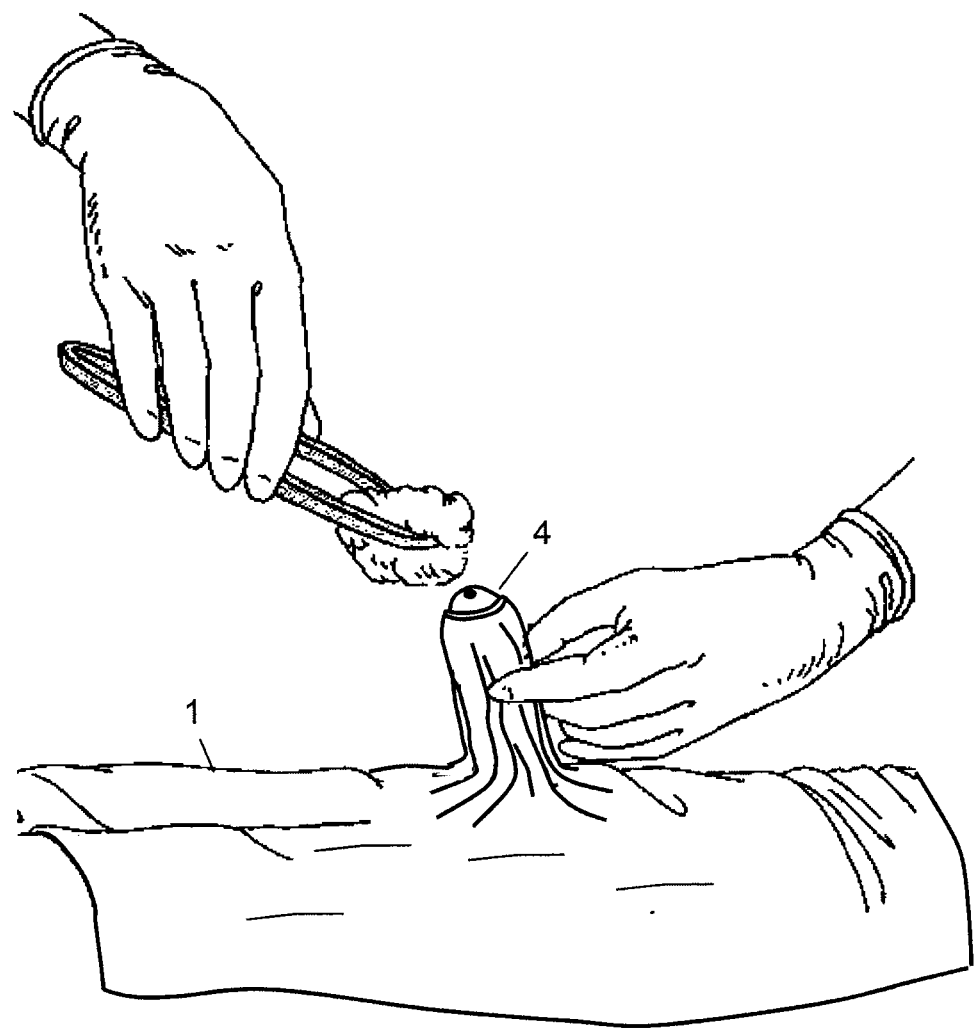
FIG. 10 shows antibacterial preparation of the patient

In FIG. 10, a sponge with antibacterial agents is applied to wipe and sterilize the meatus and small exposed portion of the glans tip. It is remarked that the area requiring treatment is very small compared to prior art, and all accessible areas from the top side of drape including the active urology area are now sterile and safely sealed from the bottom side.

Figure 11:
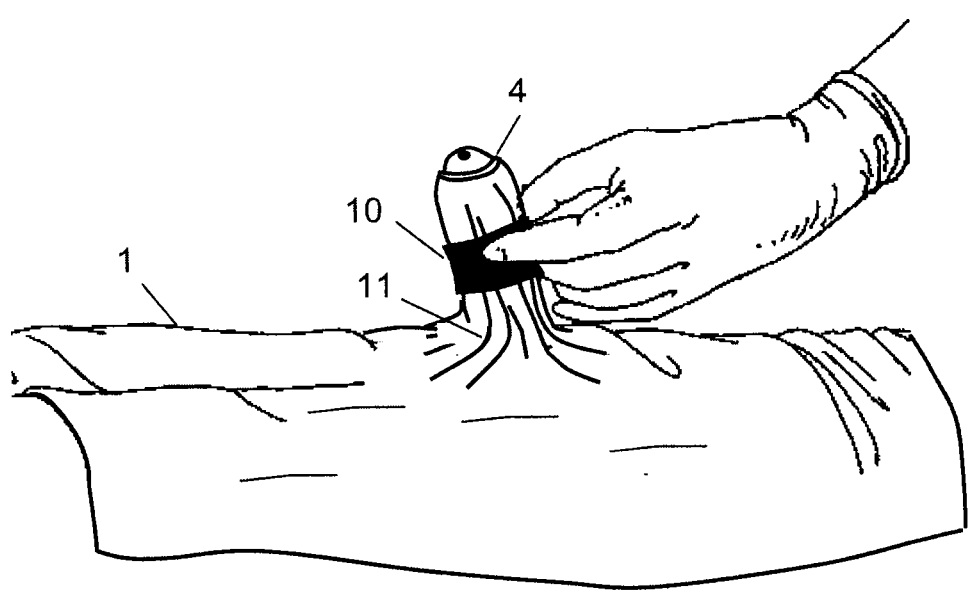
FIG. 11 shows application of the clamp to hold the drape

FIG. 11 shows a clamp 10 applied around the exterior of the penile portion of the drape 1. The clamp 10 is a sterile device that may utilize a Velcro® loop, elastic bands, or a molded medical clamp preferably made in two halves, and is applied with light pressure to not constrict the urethra. This clamp locks the drape in place to the penis, aids in sealing between above and below the drape, and generates further stiffness and position control of the shaped drape portion including longitudinal wrinkles. This allows the operator to not have to support the penis with one hand most of the time for a typical urological procedure. In order to best secure the drape 1, the clamp 10 is preferably applied right below the glans. The clamp 10 may also allow a second clamp where one clamp is positioning the penis and a second clamp may be temporary applied to close the urethra to retain medications or other purposes. The clamp 10, in a preferred embodiment of the invention, is packaged together with the inventive drape in a convenient, single-use surgical drape system.

Figure 12:
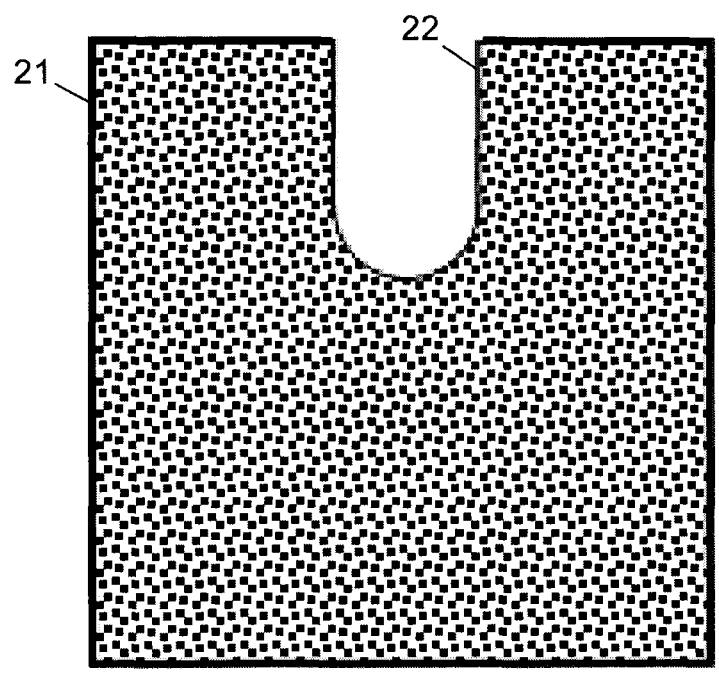
FIG. 12 shows the liquid absorbent pad

The sealed separation of a top side from a bottom side provided by this drape can now preferably also be utilized to create an improved liquid waste collection system that reduces liquids reaching the patient, the operating table or the floor. FIG. 12 shows one possible shape of a liquid absorbing pad 21 with a penile notch 22 that may be positioned on top of the drape of the invention. The illustrated shape is just one example, other shapes may include as example a ring like shape with a slit for easy removal, or one or more of rectangular shape individual pads. The pad can be made of conventional fibrous materials but may preferably utilize superabsorbent materials that allow large liquid absorption without seeping out. Antibacterial agents may be incorporated in this pad. It may also include a special exterior layer for dryness and internal gelling chemicals that convert liquid waste to semi-solid waste. Handling semi-solid medical waste is usually easier and safer than handling liquid waste that may involve open tanks, plastic bags, containers with lid, tubing and pumps, and risk for spills, leaks and personnel exposure.

Figure 13:
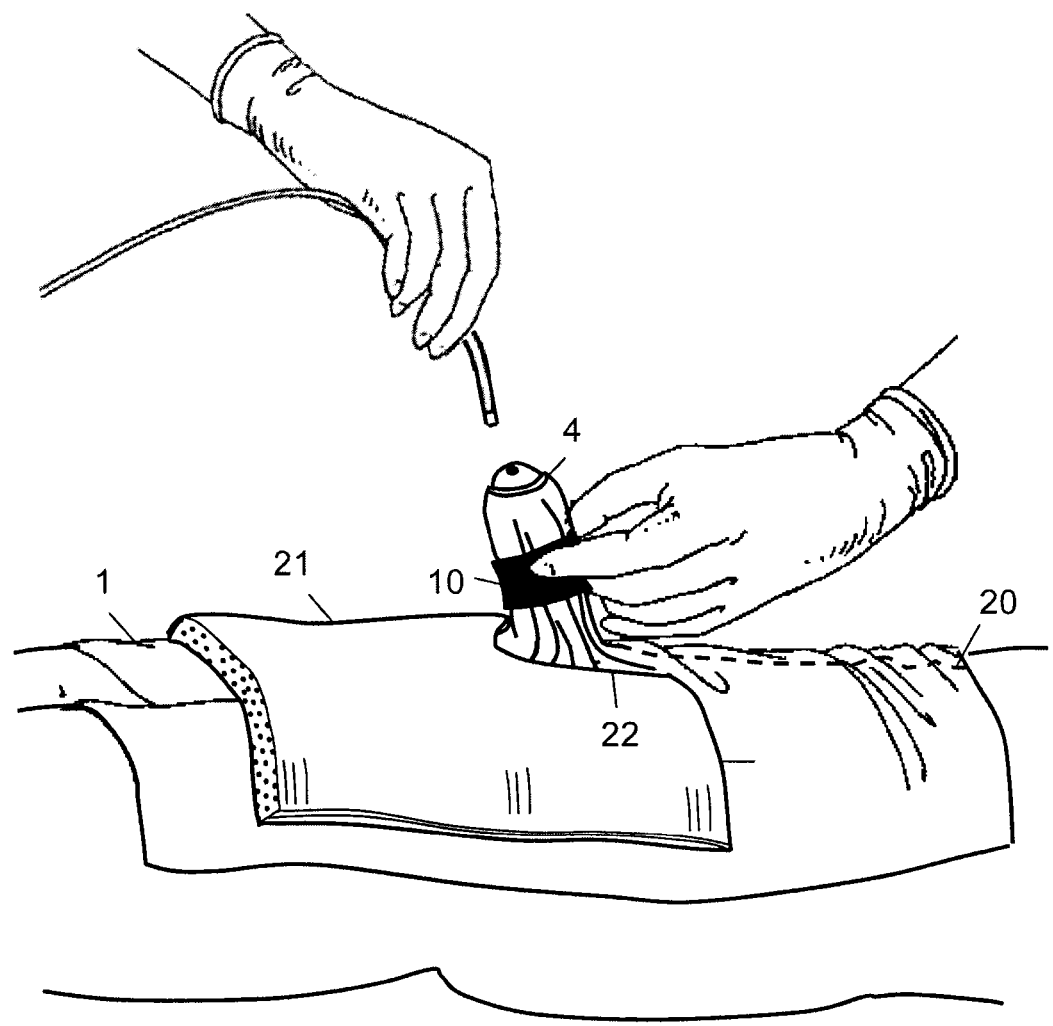
FIG. 13 shows an example of urological procedure including the invention drape.

In FIG. 13 is shown a complete drape system in conjunction with a urological procedure. The drape 1 is placed on the patient, a clamp 10 is applied around the penile area of the drape 1, and the cleaned meatus is exposed in the drape aperture 4. The operator may initially use one hand holding the penile section of the drape 1 or clamp 10 but once the critical meatus entry of urology instruments is completed, this hand can be free.

On top of the drape 1 is placed one or more absorbing pads 21 with a penile notch 22 in suitable positions to collect liquids emerging during the procedure. The sealed aperture 4 reduces chance for liquids reaching the rest of the patient body and operating table.

Upon completion of the urology procedure shown in FIG. 13 a catheter or other instruments may need to be left in place in the patient for extended time. This is simplified by the split line 20 in the drape 1 allowing it to be torn apart, and made practical due to the simple flat shape of drape 1 with no protruding molded shapes.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

What is claimed is:

1. A urological surgical drape system for partially covering a glans of a male patient while exposing a meatus area of the patient, comprising a flexible sheet having a peripheral edge and a fully flat planar shape which when positioned over the glans of the patient, the flat, planar, flexible sheet is configured so as to drape the originally fully flat planar shaped sheet around a penis in a direction parallel to the shaft of a penis of the patient, such that longitudinal stiffening wrinkles are formed by the sheet along that portion parallel to the shaft of the penis, the flexible sheet, the flexible sheet containing an internal aperture, the internal aperture being larger in size than the meatus area of the patient and smaller in size than the glans diameter of the patient and providing liquid tight sealing between a penile urethral meatus area and the surgical drape system, and a removable cover completely overlaying the aperture, the drape system including a clamp situated around the longitudinal stiffening wrinkles around the penis, the clamp configured such that the urethral meatus is not constricted and the clamp further configured to stiffen the penis.

2. The urological surgical drape of claim 1 wherein the sheet is translucent and the cover is translucent or transparent.

3. The urological surgical drape of claim 1 wherein the periphery of the flexible sheet is substantially rectangular in shape and the aperture is substantially circular.

4. The urological surgical drape of claim 1 wherein the periphery of the flexible sheet is nonrectangular in shape.

5. The urological surgical drape of claim 4 wherein the periphery of the flexible sheet is substantially circular in peripheral edge shape.

6. The urological surgical drape of claim 1 wherein the aperture is approximately centrally located in the sheet.

7. The urological surgical drape of claim 1 wherein the removable cover is adhesively attached to the sheet and includes a graspable separation tab.

8. The urological surgical drape of claim 1 wherein the flexible sheet includes a splittable tear line extending from a sheet edge to the aperture.

9. The urological surgical drape of claim 1 including a penile sealing ring positioned on the underside of the flexible sheet and surrounding the aperture.

10. The urological surgical drape of claim 9 wherein the penile sealing ring has an inside diameter that is substantially identical to the diameter of the internal aperture, or has an inside diameter that is smaller than the diameter of the internal aperture.

11. The urological surgical drape of claim 1 including indicia indicating the location of the aperture.

12. The urological surgical drape of claim 11 wherein the indicia surrounds the aperture and is spaced apart from the aperture.

13. A urological surgical drape for partially covering the glans of a male patient while exposing a meatus area of the patient, comprising a planar, fully flat, flexible sheet having a peripheral edge, the flexible sheet having a translucent central planar, fully flat section also having a peripheral edge, the translucent central section containing an internal aperture, the internal aperture being larger in size than the meatus area of the patient and smaller in size than the glans diameter of the patient and providing liquid tight sealing between a penile urethral meatus area and the surgical drape, the drape comprising a removable cover completely overlaying the aperture, the drape configured such that longitudinal stiffening wrinkles are formed when the drape is situated to surround a patient's penis, the surgical drape including a clamp configured to wrap around the longitudinal stiffening wrinkles and the penis, the clamp configured such that the urethral meatus is not constricted and the clamp further configured to stiffen the penis, the drape also comprising a second section more opaque than the translucent central section surrounding the translucent central section.

14. The urological surgical drape of claim 13 wherein the drape and the central section have peripheral edges that are rectangular in shape.

15. The urological surgical drape of claim 13 wherein the periphery of the central section is circular in shape.

16. The urological surgical drape of claim 13 wherein the periphery of the drape is nonrectangular in shape.

17. The urological surgical drape of claim 13 wherein the central section sheet is formed of a translucent plastic film and the surrounding section is formed of an opaque nonwoven material.

18. The urological surgical drape of claim 13 wherein the aperture is approximately centrally located within the drape.

19. The urological surgical drape of claim 13, further comprising a clamp configured to surround a portion of the drape covering a portion of a penis of the male patient located below the glans.

20. The urological surgical drape of claim 13 wherein the drape includes a splittable tear line extending from a drape edge to the aperture.

21. The urological surgical drape of claim 13 including a penile sealing ring positioned on the underside of the sheet and surrounding the aperture.

22. The urological surgical drape of claim 21 wherein the penile sealing ring has an inside diameter that is substantially identical to the diameter of the internal aperture, or has an inside diameter that is smaller than the diameter of the internal aperture.

23. The urological surgical drape of claim 13 including indicia indicating the location of the aperture.

24. The urological surgical drape of claim 23 wherein the indicia surrounds the aperture and is spaced apart from the aperture.

25. A method for preparing a male patient for a urological procedure requiring the covering of portions of the patient's genital area include portions of a penis including a glans area while exposing a urethral meatus area of the patient and limiting the exposed area to an area less than a diameter of the patient's glans comprising the steps of:
   (1) Laying a urological surgical drape for a male patient comprising a fully flat, planar, flexible sheet containing an internal aperture, the internal aperture being larger in size than the meatus area of the patient and smaller in size than a diameter of the patient's glans, a penile sealing ring to provide a liquid tight seal between the urethral meatus and the urological surgical drape, and a removable aperture cover completely overlaying the aperture, over the genital area of the patient with the aperture cover facing away from the patient;
   (2) Positioning the surgical drape such that the aperture and aperture cover are substantially centered over the urethral meatus area of the patient and arranging the surgical drape such that it extends downward from the aperture and is substantially parallel to a shaft of the penis, such an arrangement forming wrinkles longitudinally along that portion of the drape parallel to the shaft of the penis, before extending across an area comprising the lower abdomen of the patient;
   (3) Applying a clamp to the longitudinal wrinkles such that the clamp surrounds at least a portion of the shaft of the penis, the clamp configured to hold the drape in place and stiffen the penis; and
   (4) Removing the aperture cover to expose the urethral meatus in approximately the center of the aperture.

26. The method of claim 25 further comprising the step of: (5) applying an antibacterial agent to the exposed areas of the penis of the patient.

27. The method of claim 25 further comprising the step of: (4) applying a penile clamp positioned below the glans of the patient and on an outer surface of that portion of the drape in which wrinkles have been formed for holding the surgical drape in position around the penis of the patient without constricting the urethra.

28. The method of claim 25 wherein an absorbent sheet having a penile opening is applied over the surgical drape.

29. A method for preparing a male patient for a urological procedure requiring the covering of portions of the patient's genital area include portions of a penis while exposing a urethral meatus area of the patient and limiting the exposed area to an area less than a diameter of the patient's glans comprising the steps of:
   (1) Laying a urological surgical drape for a male patient comprising a fully planar, flat, flexible sheet, the sheet having a translucent central section containing an internal aperture, the internal aperture being larger in size than the meatus area of the patient and smaller in size than the glans diameter of the patient, a penile sealing ring configured to provide a liquid tight seal between the urological surgical drape and urethral meatus area, and with a removable aperture cover completely overlaying the aperture, and a second section more opaque than the translucent central section, the second section surrounding the translucent central section, over the genital area of the patient with the aperture cover facing away from the patient;

(2) Positioning the surgical drape such that the aperture substantially centered over the urethral meatus area of the patient and arranging the surgical drape such that it extends downward from the covered aperture and is substantially parallel to a shaft of the penis, such an arrangement forming wrinkles longitudinally along that portion of the drape parallel to the shaft of the penis, the wrinkles configured to stiffen the penis, before extending across an area comprising the lower abdomen of the patient;

(3) applying a penile clamp position below the glans of the patient and on an outer surface of that portion of the drape in which wrinkles have been formed for holding he surgical drape in position around the penis of the patent, the clamp configured so as not to constrict the urethra; and (4) Removing the aperture cover to expose the urethral meatus in approximately the center of the aperture.

30. The method of claim 29 wherein (4) a penile clamp is positioned below the glans of the patient and on an outer surface of that portion of the drape in which wrinkles have been formed for holding the surgical drape in position around the penis of the patient without constricting the urethra.

31. The method of claim 29 wherein an absorbent sheet having a penile opening is applied over the surgical drape.

32. A method for preparing a male patient for a urological procedure requiring the covering of portions of the patient's genital area include portions of a penis while exposing a urethral meatus area of the patient and limiting the exposed area to an area less than a diameter of the patient's glans comprising (1) Laying a urological surgical drape for a male patient comprising a planar, fully flat, flexible sheet, the sheet having a translucent central section containing an internal aperture, the internal aperture being larger in size than the meatus area of the patient and smaller in size than the glans diameter of the patient a penile sealing ring configured to provide a liquid tight seal between the drape and urethral meatus area, and with a removable cover completely overlaying the aperture, and a second section more opaque than the translucent central section, the section surrounding the translucent central section, and including indicia indicating the location of the aperture, over the genital area of the patient with the aperture cover facing away from the patient;

(2) Positioning the surgical drape such that the aperture substantially centered over the urethral meatus area of the patient and arranging the surgical drape such that it extends downward from the aperture and is substantially parallel to a shaft of the penis, such an arrangement forming wrinkles longitudinally along that portion of the drape parallel to the shaft of the penis, before extending across an area comprising the lower abdomen of the patient;

(3) applying a penile clamp position below the glans of the patient and on an outer surface of that portion of the drape in which wrinkles have been formed for holding he surgical drape in position around the penis of the patent, the clamp configured so as not to constrict the urethra; and (4) Removing the aperture cover to expose the urethral meatus in approximately the center of the aperture and allowing the sealing ring to sealingly engage the glans area.

33. The method of claim 32 wherein (4) a clamp is applied to a portion of the longitudinal wrinkles, where the clamp at least partially surrounds the shaft of the penis.

\* \* \* \* \*